(12) United States Patent
Sims

(10) Patent No.: US 6,331,272 B1
(45) Date of Patent: Dec. 18, 2001

(54) METHOD AND MEMBRANE SYSTEM FOR STERILIZING AND PRESERVING LIQUIDS USING CARBON DIOXIDE

(75) Inventor: Marc Sims, Berkeley, CA (US)

(73) Assignee: Porocrit, L.L.C., Berkeley, CA (US)

( * ) Notice: Subject to any disclaimer, the term of this patent is extended or adjusted under 35 U.S.C. 154(b) by 0 days.

(21) Appl. No.: 09/228,925

(22) Filed: Jan. 12, 1999

(51) Int. Cl.$^7$ ....................................... A61L 2/00
(52) U.S. Cl. .................. 422/28; 99/495; 422/1; 422/31; 422/33; 422/41; 422/48; 422/256; 422/905; 426/330; 426/424; 426/425
(58) Field of Search .................. 422/28, 1, 31, 422/33, 41, 48, 256, 905; 426/330, 330.3, 335, 424–425; 99/495; 210/634, 644, 648, 321.6, 321.64, 321.79

(56) References Cited

U.S. PATENT DOCUMENTS 5,490,884 * 2/1996 Robinson et al. ................. 95/45

* cited by examiner

Primary Examiner—Krisanne Thornton
(74) Attorney, Agent, or Firm—Harris Zimmerman

(57) ABSTRACT

Microorganisms are destroyed and enzymes can be inactivated in liquids, such as juices for example, by continuously flowing the liquid and continuously flowing pressurized dense $CO_2$ along flow paths which are separated by membrane having minute pores at which the flows contact each other in a nondispersive manner. Pressures in the two flow paths are equalized and the dense $CO_2$ flow is continuously recirculated without depressurization. Contact between the flows can be maximized by using a plurality of parallel hollow fiber porous membranes with one of the flows being directed into the hollow fibers and the other of the flows being directed along exterior surfaces of the fibers. The process does not adversely affect properties of the liquid, such as taste, aroma and nutritional content, as heating of the liquid to a high temperature is unnecessary.

18 Claims, 3 Drawing Sheets

METHOD AND MEMBRANE SYSTEM FOR STERILIZING AND PRESERVING LIQUIDS USING CARBON DIOXIDE

TECHNICAL FIELD

This invention relates to the sterilization and preservation of liquids such as liquid foods for example and more particularly to methods and apparatus for inactivating microbes and/or enzymes in liquids by exposure of the liquids to dense carbon dioxide.

BACKGROUND OF THE INVENTION

Preservation of many liquids such as juices or other liquid foods or medicines requires killing of microbes, such as bacteria, viruses and spores, in the liquid. It may also be necessary to inactivate enzymes which can catalyze undesired reactions in the liquid. Pasteurization is the most commonly used process for the purpose. Pasteurization requires heating of the liquid to temperatures which can degrade the quality of the liquid. Heating of liquid foods for example can adversely affect the taste and nutritional quality of the food.

It has heretofore been recognized that liquids can be sterilized and preserved by contacting the liquids with pressurized dense $CO_2$ (carbon dioxide). The process does not require heating of the liquids to damaging temperatures. Prior processes and equipment for this purpose have not been ideally suited for commercial operation.

Some prior processes are static in that the dense $CO_2$ and liquid are simply allowed to stand together in a pressure vessel for a period of time. The production rate of treated liquid is undesirably low. Other prior processes are dynamic in that a forced dispersion of a flow of dense $CO_2$ into a flow of the liquid is brought about in a column which contains conventional packing such as rashig rings or a frit. Dispersive processes of this kind increase the production rate of treated liquid by creating a greater interfacial contact area between the dense $CO_2$ and liquid than is present in the static processes. A still greater interface area between the liquid and dense $CO_2$, in a given volume of flow, would be advantageous.

Dispersive processes of the above discussed kind are also subject to other problems. For example, emulsification of the liquid and dense $CO_2$ can occur necessitating further steps to break the emulsion. Processing of liquids of certain densities may not be practical as a density difference between the liquid and dense $CO_2$ is needed in order to separate the two. Fouling of components within the processing vessel may occur if the liquid contains suspended particulate matter.

The present invention is directed to overcoming one or more of the problems discussed above.

SUMMARY OF THE INVENTION

In one aspect, the invention provides a method for preserving a liquid by exposure of the liquid to pressurized dense carbon dioxide. Steps in the method include directing a flow of the liquid along a liquid flow path which extends along a first surface of a porous membrane and directing a flow of the dense carbon dioxide along a carbon dioxide flow path which extends along an opposite surface of the membrane including contacting the liquid and pressurized carbon dioxide at pores in the membrane. Further steps include recirculating the flow of dense carbon dioxide through the carbon dioxide flow path while maintaining the dense carbon dioxide in the pressurized state throughout the recirculation.

In another aspect of the invention, wherein the liquid has a constituent that is soluble in dense carbon dioxide and which becomes a solute in the dense carbon dioxide during passage of the carbon dioxide along the membrane, the method includes the further steps of establishing saturation of the dense carbon dioxide with the solute and maintaining saturation of the dense carbon dioxide with the solute during the recirculation of the dense carbon dioxide.

In another aspect the invention provides apparatus for preserving liquids by exposure of the liquids to pressurized dense carbon dioxide. Components of the apparatus include a membrane contactor having a liquid flow path and a carbon dioxide flow path therein. The flow paths are separated by porous membrane having pores which enable contact of a liquid flowing in the liquid flow path with carbon dioxide flowing in the carbon dioxide flow path. A liquid pressurizing pump has an outlet communicated with the membrane contactor to direct liquid into the liquid flow path. A dense carbon dioxide recirculation pump has an inlet communicated with the membrane contactor to receive pressurized dense carbon dioxide which flows out of the carbon dioxide flow path and has an outlet through which the pressurized dense carbon dioxide is returned to the carbon dioxide flow path.

In sill another aspect of the invention, the membrane contactor has a shell and a plurality of hollow fiber porous membranes extend in a generally parallel direction within the shell. One of the liquid flow path and the carbon dioxide flow path extends through the lumen regions of the hollow fiber porous membranes and the other of the flow paths extends along exterior surfaces of the hollow fiber porous membranes.

The invention enables nondispersive contacting of flows of a liquid and dense $CO_2$ in which the area of contact of the two flows in a given volume is far greater than in prior static or dispersive processes. The production rate of sterilized liquid is thereby increased. Emulsion formation does not occur as dispersion of the $CO_2$ flow into the liquid flow is not required. It is not necessary that there be a density difference between the liquid and dense $CO_2$ in order to separate the two. The invention does not require components which may be subject to fouling by suspended particulates in the liquid. The process can be run continuously and isobarically thereby saving energy and equipment costs.

The invention, together with further aspects and advantages thereof, may be further understood by reference to the following description of the preferred embodiment and by reference to the accompanying drawings.

DETAILED DESCRIPTION OF THE PREFERRED EMBODIMENT

The invention is applicable to the treatment of any of the aqueous liquids which are known to be sterilizable by being contacted with dense carbon dioxide gas ($CO_2$) for a period of time sufficient to destroy microorganisms in the liquid. These are typically liquid foods such as fruit or vegetable juices for example or liquid medicines although other types of liquid may also be treated. It is believed that microorganism destruction occurs as a result of a temporary formation of carbonic acid in the liquid. It is also known that temporary exposure to dense $CO_2$ can be used to inactivate enzymes which may catalyze undesired changes in a liquid over a period of time.

Figure 1:
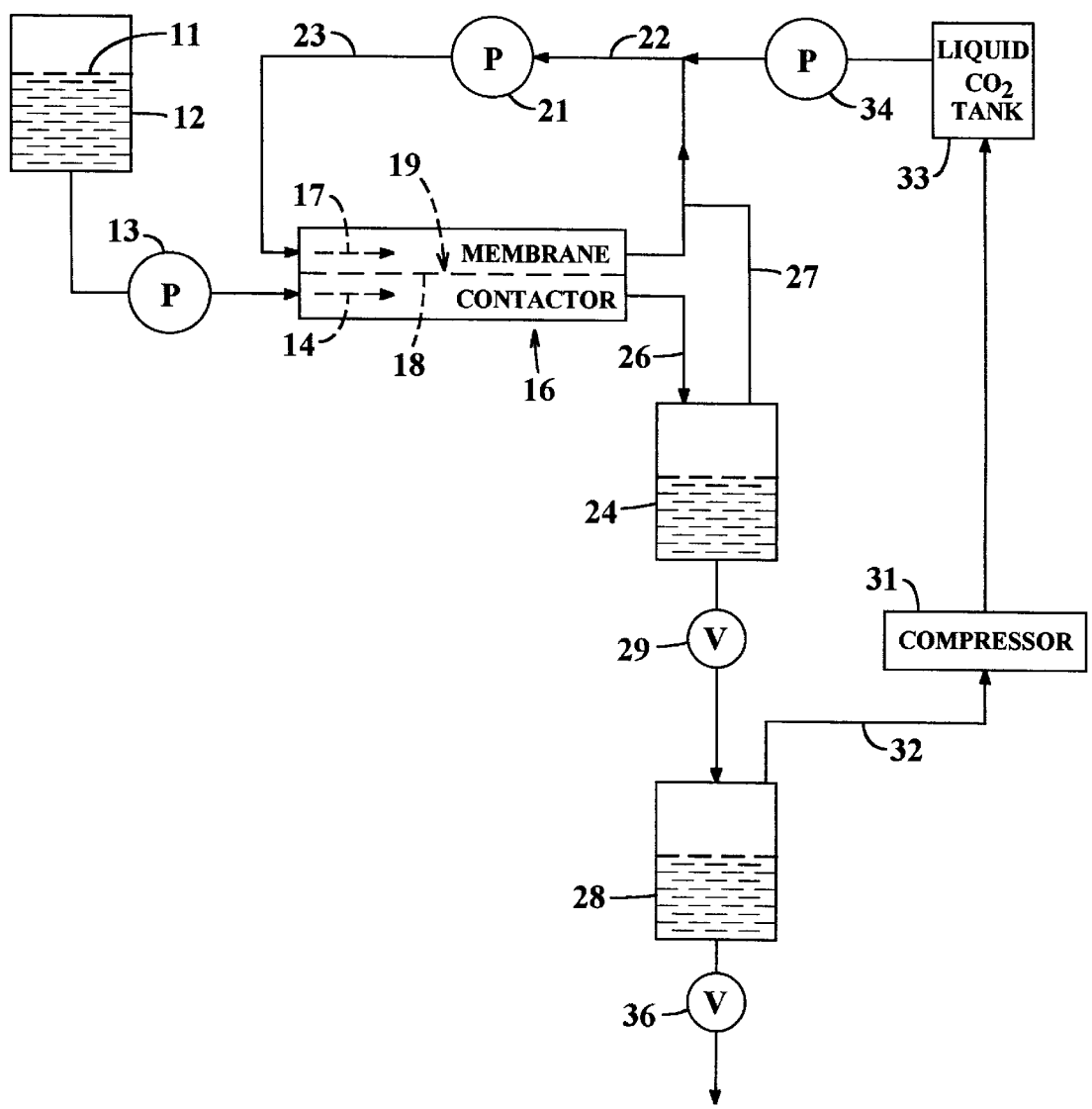
FIG. 1 is a schematic diagram depicting apparatus for sterilizing and preserving liquids in accordance with the invention.

Referring initially to FIG. 1 of the drawings, the untreated liquid 11 which may be initially contained in an untreated liquid tank 12 is pressurized by a liquid feed pump 13 and delivered to a liquid flow path 14 situated within a membrane contactor 16. A preferred detailed construction for the membrane contactor 16 will hereinafter be described. Within the membrane contactor 16, the liquid flow path 14 is separated from a dense $CO_2$ flow path 17 by porous membrane 18. Contact of the liquid 11 with dense $CO_2$ occurs at minute pores 19 which penetrate through the membrane 18. The dense $CO_2$ flow is continually recirculated through flow path 17 by a recirculation pump 21 having an inlet conduit 22 and an outlet conduit 23 connected to opposite ends of the membrane contactor 16. The dense $CO_2$ is maintained in its pressurized condition throughout the recirculation process.

Pressurization of the dense $CO_2$ flow and the liquid flow within membrane contactor 16 may typically be in the range from about 1000 to about 3000 psi and operating temperature may be from about 20 to about 400° C. although operation outside of these ranges is also possible. Dwell time of the liquid 11 within the membrane contactor 16 will vary for different liquids and can easily be determined for any particular liquid by examining the treated liquid to ascertain if undesired microorganisms have been destroyed.

The outflow of pressurized treated liquid from flow path 14 of membrane contactor 16 is delivered to a first receiver tank 24 through an outlet flow conduit 26. Equalization of the pressure within the two flow paths 14 and 17 within membrane contactor 16 is assured by a pressure equalization conduit 27 which communicates the $CO_2$ flow path 17 with the interior of the first receiver tank 24. Thus there is no significant pressure gradient between the two flow paths 14 and 17 which might act to force transfer of fluid therebetween.

Treated fluid from the first receiver tank 24 is continuously released into a second receiver tank 28 through a pressure reducer valve 29. The second receiver tank 28 is a low pressure tank and is preferably maintained at atmospheric pressure. $CO_2$ which has been acquired by the treated liquid separates out of the liquid within the low pressure tank 28. A $CO_2$ recovery compressor 31 has an intake conduit 32 communicated with the top region of the low pressure tank 28 and acts to liquefy the $CO_2$ which separates out in the tank 28. Compressor 31 delivers the recovered $CO_2$ to a liquid $CO_2$ storage tank 33. Make up $CO_2$ is transferred from the storage tank 33 to recirculation pump 21, through a make up pump 34, at a rate sufficient to maintain the desired operating pressure within the flow paths 14 and 17 of membrane contactor 16. Thus the process consumes only the amount of $CO_2$ that may be allowed to leave the processing apparatus in the treated liquid.

Treated liquid is drained from the base of the low pressure tank 28 into appropriate containers through another valve 36.

Membrane contactors 16 of the type used in the practice of the present invention are sometimes used to extract desired constituents from a liquid when the constituent is soluble in dense $CO_2$. In those processes the solute is separated from the $CO_2$ flow by depressuring the $CO_2$ in an expansion chamber or the like. Unwanted extraction of any significant amount of such a solute need not occur in the practice of the present invention if the dense $CO_2$ flow is maintained in its pressurized condition throughout the recirculation process. Under this condition, the dense $CO_2$ flow is quickly saturated with constituents of the liquid that are soluble in $CO_2$. The constituents of the liquid which are soluble in $CO_2$ largely stay in the liquid after the recirculating $CO_2$ flow becomes saturated with them. For example, fruit juices retain their aroma.

Figure 2:
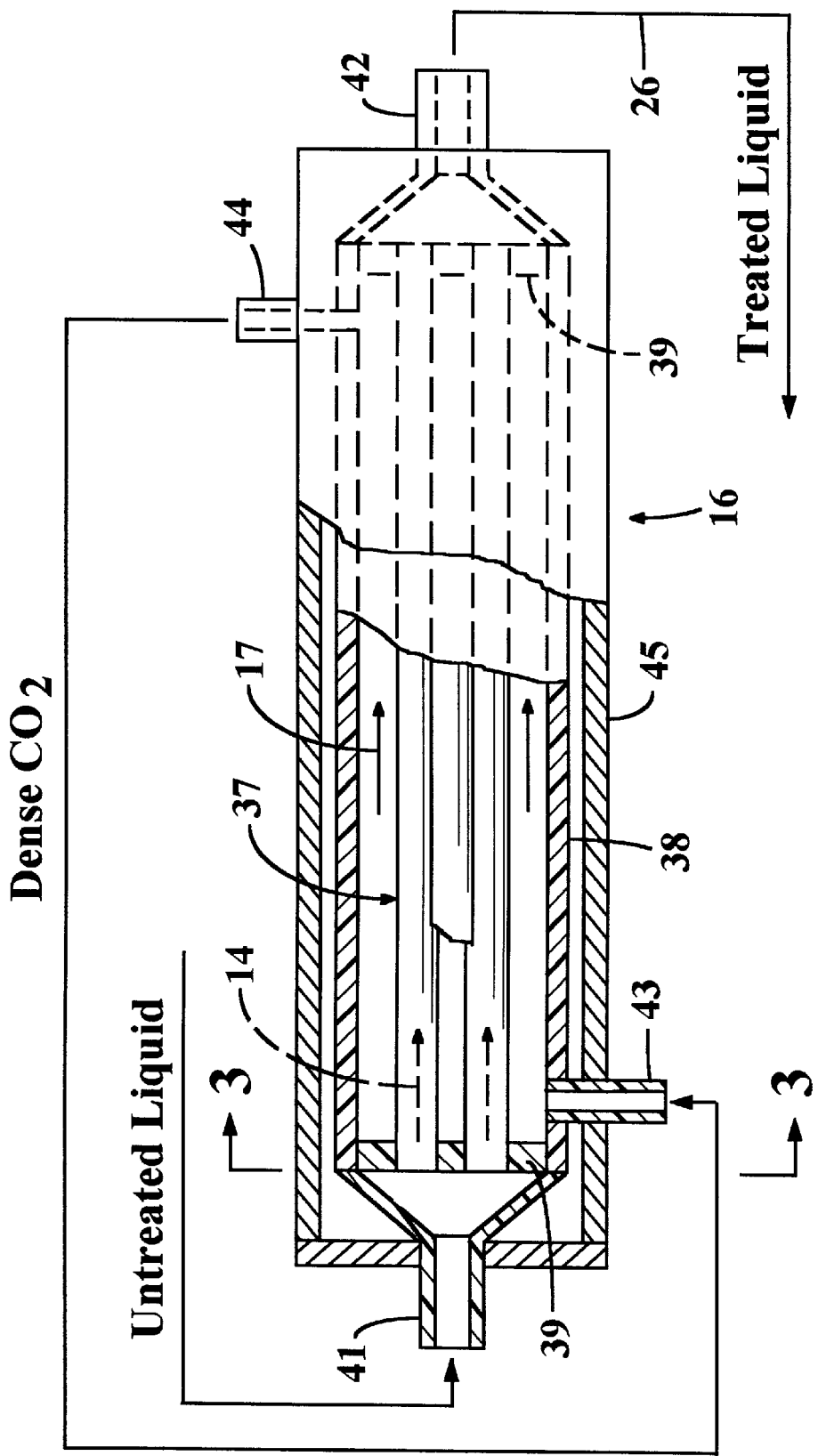
FIG. 2 is a broken out side view of a preferred form of membrane contactor for use in the apparatus of FIG. 1.
Figure 3:
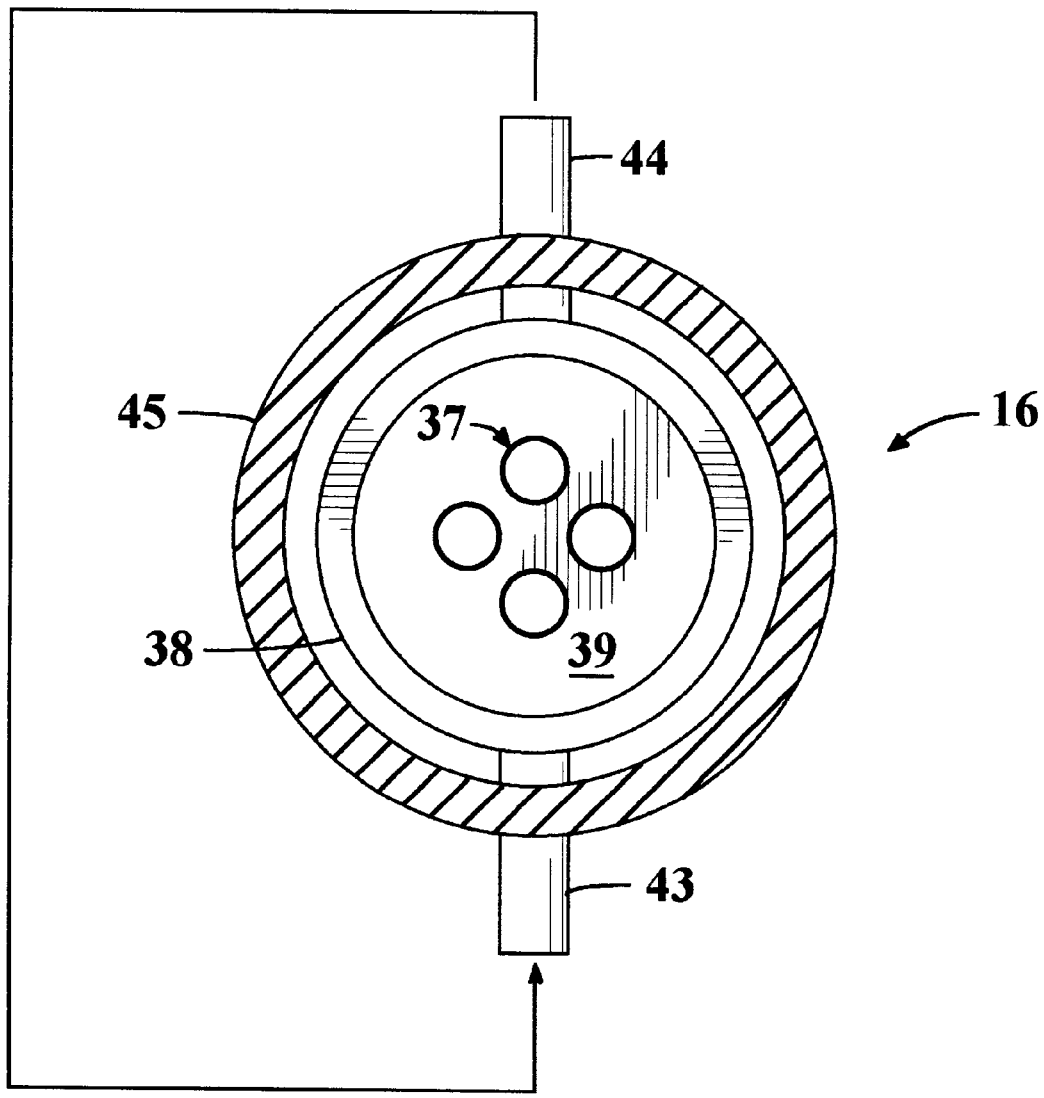
FIG. 3 is a cross section view of the membrane contactor taken along line 3-3 of FIG. 2.

The membrane contactor 16 may be of any of various other forms but is preferably of the type depicted in FIGS. 2 and 3 which provides an extremely large interface area of contact between the liquid and dense $CO_2$. The contact area may be as much as 100 times greater in a given volume of liquid than is present in contactors of the hereinbefore discussed static or dynamic dispersive types.

The membrane 18 in a contactor 16 of this preferred type is a plurality of tubular hollow fiber porous membranes 37. The fiber membranes 37 of this embodiment are linear and extend longitudinally, in a generally parallel and slightly spaced apart relationship, within a tubular shell 38. Ends of the fiber membranes 37 extend through end closures 39 at each end of shell 38. A liquid inlet port member 41 at one end of shell 38 acts as a manifold which directs incoming untreated liquid into the adjacent ends of the hollow fiber membranes 37. A similar liquid outlet port member 42 at the other end of the shell 38 receives liquid which has traveled through the membranes 37 and channels the liquid into the previously described liquid outlet conduit 26. Thus the lumens of the hollow fiber membranes 37 jointly provide the liquid flow path 14 of the membrane contactor 16 in this example of the invention.

A tubular dense gas flow inlet port 43 communicates with the interior of shell 38 at one end of the shell and a dense gas outlet port 44 communicates with the interior of the shell at the opposite end thereof. Thus portions of the interior of shell 38 which are outside of the hollow fiber membranes 37 provide the dense gas flow path 17 of the membrane contactor 16 in this embodiment of the invention. Ports 38 and 39 and port members 36 and 37 protrude from a housing 45 which encloses the shell 33.

The above described porting arrangements can be reversed so that the incoming untreated liquid flows into one of the ports 43 and 44 and out of the other while the dense $CO_2$ is directed into one of the port members 41 and 42 and flows out of the other port member. In this alternate arrangement the lumens of the fiber membranes 37 function as the dense $CO_2$ flow path of the membrane contactor 13 while the interior region of shell 38 that is outside of the membranes functions as the liquid flow path of the contactor.

Passage of liquid through the pores of the fiber membranes 37 is inhibited by using a membrane material which is not wetted by the liquid and by limiting the size of the pores. In the case of aqueous liquids the membrane is formed of hydrophobic material such as polypropylene plastic as one example. The membrane material may be of a hydrophilic type if the liquid is an oil or other hydrophobic fluid. Pore diameter may vary depending on the characteristics of the particular membrane material and liquid but will typically be in the range from about 0.001 micron to about 1 micron if the wall thickness of the membranes is within the range from about 0.005 mm to about 3 mm. In general it is preferable to select the largest pore size which is observed to inhibit passage of the particular liquid through the membrane as this maximizes the interface area of the liquid and dense $CO_2$.

A membrane contactor 16 of this type which is designed for commercial operation will typically contain more of the hollow fiber membranes 37 than are depicted in FIGS. 2 and 3. Membrane contactors 16 which were used in the example of the practice of the method that is hereinafter described contained 120 such hollow fiber membranes 37. The hollow fiber membranes 37 were formed of polypropylene plastic and had an inside diameter of 0.6 mm, a wall thickness of 200 micrometers and were 40 cm long. The average size of the pores of the hollow fiber membranes 37 was 0.2 micrometers and the porosity of the fiber walls was 70%, porosity being the percentage of the membrane wall that is occupied by pores. It should be recognized that these specific materials and dimensions are presented for purposes of example and that other materials and dimensioning are also workable.

Example of the Method

Fresh radish juice was contacted with high pressure $CO_2$ while being pumped through two membrane contactors 16 of the type which has been hereinbefore described. The two membrane contactors 16 were connected in series relationship and thus the radish juice passed sequentially through the two contactors. Flow rate was 4.2 g/min. The system was maintained at 200 bar pressure and 24° C. temperature during the 24 minute experiment. Average residence time of the juice in the membrane contactors 16 was 6 minutes. The juice was retained in a raffinate receiver 24 for approximately another ten minutes before being drained into a beaker.

The dense $CO_2$ treatment substantially reduced the microbial content of the juice as measured in plate counts which were as follows:

| PLATE COUNTS OF RADISH JUICE | | |
| --- | --- | --- |
|  | Yeast | Total |
| Before $CO_2$ | 30 per g | 2910 per g |
| After $CO_2$ | less than 10 per g | less than 10 per g |

(Less than 10 per g is equivalent to nondetectable)

It has also been observed that garlic puree processed in accordance with the invention does not change aroma as rapidly as the untreated puree. The aroma change is catalyzed by the enzyme allinase, among others. Fresh ginger root juice standing at room temperature in a sealed bottle has been observed to begin fermenting several days before the same juice which has been exposed to dense $CO_2$ in a membrane contactor of the previously described kind.

While the invention has been described with reference to a specific embodiment for purposes of example, many modifications and variations are possible and it is not intended to limit the invention except as defined in the following claims:

1. A method for preserving a liquid by exposure of the liquid to pressurized dense carbon dioxide comprising the steps of:
   directing the flow of said liquid along a liquid flow path which extends along a first surface of a porous membrane and directing a flow of said pressurized dense carbon dioxide along a separate carbon dioxide flow path which extends along an opposite surface of said porous membrane including contacting said liquid and pressurized dense carbon dioxide at pores in said membrane, and
   recirculating said flow of pressurized dense carbon dioxide through said carbon dioxide flow path including maintaining the pressurized dense carbon dioxide in the pressurized dense condition throughout the recirculation thereof.

2. The method of claim 1 including the further step of maintaining substantially the same elevated pressure in said liquid flow path and in said carbon dioxide flow path.

3. The method of claim 1 wherein said liquid has a constituent that is soluble in dense carbon dioxide and which becomes a solute in said dense carbon dioxide during passage of said dense carbon dioxide along said carbon dioxide flow path, including the further step of establishing saturation of said dense carbon dioxide with said solute and maintaining said saturation of said dense carbon dioxide with said solute during said recirculation of said dense carbon dioxide.

4. The method of claim 1 including the further steps of continuously receiving liquid from said liquid flow path in a first receiver tank and maintaining said first receiver tank at a pressure which is substantially the same as the pressure within said carbon dioxide flow path.

5. The method of claim 4 including the further steps of depressurizing said liquid while continuously releasing the liquid from said first receiver tank into a second receiver tank, recovering low pressure carbon dioxide from said second receiver tank, recompressing the recovered low pressure carbon dioxide and returning recompressed carbon dioxide to said carbon dioxide flow path.

6. The method of claim 1 wherein said liquid flow path and carbon dioxide flow path are defined by a plurality of hollow fiber porous membranes, including directing one of said flow of liquid and said flow of dense carbon dioxide through into said hollow fiber porous membranes and directing the other of said flow of liquid and said flow of dense carbon dioxide along external surfaces of said hollow fiber porous membranes.

7. The method of claim 1 including continuously flowing said liquid along said liquid flow path and continuously flowing said pressurized dense carbon dioxide along said carbon dioxide flow path.

8. The method of claim 1 including contacting said liquid and said dense carbon dioxide for a period sufficient to sterilize said liquid.

9. The method of claim 1 including contacting said liquid and said dense carbon dioxide for a period sufficient to inactivate an enzyme in said liquid.

10. Apparatus for preserving liquids by exposure of the liquids to pressurized dense carbon dioxide comprising:
    a membrane contractor having a liquid flow path and a pressurized dense carbon dioxide flow path therein, said flow paths being separated from each other by porous membrane having pores which enable contact of a liquid flowing in said liquid flow path with pressurized dense carbon dioxide flowing in the carbon dioxide flow path,
    a liquid pressurizing pump having an outlet communicated with said membrane contactor to direct liquid into said liquid flow path, and
    a pressurized dense carbon dioxide recirculation pump having an inlet communicated with said membrane contactor to receive pressurized dense carbon dioxide which flows out of said carbon dioxide flow path and having an outlet communicated with said membrane contactor to return the pressurized dense carbon dioxide to said pressurized dense carbon dioxide flow path.

11. The apparatus of claim 10 wherein said membrane contactor includes a shell and a plurality of hollow fiber porous membranes extending in a generally parallel direction within said shell, and wherein one of said flow paths extends through lumen regions of said hollow fiber porous membranes and the other of said flow paths extends along exterior surfaces of said hollow fiber porous membranes.

12. The apparatus of claim 10 further including a first receiver tank having an inlet communicated with said membrane contactor to receive liquid from said liquid flow path, further including a pressure equalizing flow conduit communicating said dense carbon dioxide flow path with said first receiver tank.

13. The apparatus of claim 12 further including a second receiver tank having an inlet communicated with said first receiver tank to receive liquid therefrom through a pressure reducer.

14. The apparatus of claim 13 further including a liquid carbon dioxide storage tank, means for releasing carbon dioxide from said storage tank to said carbon dioxide flow path to maintain a particular operating pressure therein, and a compressor recovering low pressure carbon dioxide from said second receiver tank and which liquefies the recovered carbon dioxide, said compressor having an outlet communicated with said liquid carbon dioxide storage tank.

15. The apparatus of claim 10 wherein said membrane contactor includes a tubular shell and a plurality of substantially parallel hollow fiber porous membranes extending in a generally axial direction therein and wherein one of said flow paths extends through lumen regions of said hollow fiber porous membranes and the other of said flow paths extends along exterior surfaces of said hollow fiber porous membranes further including:
   a first receiver tank having an inlet communicated with said membrane contactor to receive liquid from said liquid flow path,
   a pressure equalizing flow conduit communicating said dense carbon dioxide flow path with said first receiver tank, and
   a second receiver tank having an inlet communicated with said first receiver tank to receive treated liquid therefrom through a pressure reducer.

16. A method for sterilizing a liquid by exposure of the liquid to pressurized dense carbon dioxide comprising the steps of:
   directing a flow of said liquid along a liquid flow path which extends along a first surface of a porous membrane and directing a flow of said pressurized dense carbon dioxide along a separate carbon dioxide flow path which extends along an opposite surface of said porous membrane including contacting said liquid and pressurized dense carbon dioxide at pores in said membrane, and
   recirculating said flow of pressurized dense carbon dioxide through said carbon dioxide flow path including maintaining the pressurized dense carbon dioxide flow in the pressurized dense condition throughout the recirculating thereof.

17. Apparatus for sterilizing liquids by exposure of the liquids to pressurized dense carbon dioxide comprising:
   a membrane contactor having a liquid flow path and a pressurized dense carbon dioxide flow path therein, said flow paths being separated from each other by porous membrane having pores which enable contact of a liquid flowing in said liquid flow path with pressurized dense carbon dioxide flowing in the carbon dioxide flow path,
   a liquid pressurizing pump having an outlet communicated with said membrane contactor to direct liquid into said liquid flow path, and
   a pressurize dense carbon dioxide recirculating pump having an inlet communicated with said membrane contactor to receive pressurized dense carbon dioxide which flows out of said carbon dioxide flow path and having an outlet communicated with said membrane contactor to return the pressurized dense carbon dioxide to said pressurized dense carbon dioxide flow path.

18. A method for sterilizing a liquid by exposure of the liquid to pressurized dense carbon dioxide, which liquid contains at least one constituent which is soluble in said pressurized dense carbon dioxide, comprising the steps of:
   directing a flow of said liquid along a liquid flow path which extends along a first surface of a porous membrane and directing said pressurized dense carbon dioxide to an opposite surface of said porous membrane including contacting said liquid and pressurized dense carbon dioxide at pores in said membrane to sterilize said liquid and to saturate said pressurized dense carbon dioxide with said soluble constituent of said liquid, and
   maintaining the pressurized dense carbon dioxide at said opposite side of said porous membrane in the saturated condition during continued sterilization of said flow of liquid.

* * * * *